United States Patent
Niwayama et al.

(10) Patent No.: US 9,433,352 B2
(45) Date of Patent: Sep. 6, 2016

(54) OPTICAL MEASURING DEVICE

(75) Inventors: Masatsugu Niwayama, Hamamatsu (JP); Naohiro Kanayama, Hamamatsu (JP); Kazunao Suzuki, Hamamatsu (JP)

(73) Assignees: National University Corporation Shizuoka University, Shizuoka-shi (JP); National University Corporation Hamamatsu University School of Medicine, Hamamatsu-shi (JP)

( * ) Notice: Subject to any disclaimer, the term of this patent is extended or adjusted under 35 U.S.C. 154(b) by 431 days.

(21) Appl. No.: 14/001,384

(22) PCT Filed: Feb. 23, 2012

(86) PCT No.: PCT/JP2012/054473
§ 371 (c)(1),
(2), (4) Date: Oct. 21, 2013

(87) PCT Pub. No.: WO2012/115210
PCT Pub. Date: Aug. 30, 2012

(65) Prior Publication Data
US 2014/0039284 A1    Feb. 6, 2014

(30) Foreign Application Priority Data
Feb. 23, 2011   (JP) .................. 2011-037444

(51) Int. Cl.
*A61B 5/1455*   (2006.01)
*A61B 5/00*   (2006.01)
(Continued)

(52) U.S. Cl.
CPC ......... *A61B 5/0059* (2013.01); *A61B 5/14551* (2013.01); *A61B 5/4872* (2013.01);
(Continued)

(58) Field of Classification Search
None
See application file for complete search history.

(56) References Cited

U.S. PATENT DOCUMENTS

2004/0267139 A1   12/2004  Kanayama et al.
2009/0209836 A1*  8/2009  Niwayama ......... A61B 5/14551
                                                600/324

FOREIGN PATENT DOCUMENTS

| JP | H06103257 | 12/1994 |
| JP | 2517858 B2 | 7/1996 |
| JP | 2000136997 A | 5/2000 |
| JP | 2003-144439 A | 5/2003 |

(Continued)

OTHER PUBLICATIONS

International Preliminary Report on Patentability for PCT/JP2012/054473 dated Feb. 23, 2011.

*Primary Examiner* — Tse Chen
*Assistant Examiner* — Marjan Fardanesh
(74) *Attorney, Agent, or Firm* — Marshall, Gerstein & Borun LLP

(57) ABSTRACT

An accurate measurement can be made of the light absorbance of deep layer tissue such as in a human body or a fruit. The thickness of fat is computed. A first specific distance and a second specific distance corresponding to the computed fat thickness are computed based a predetermined relationship between the fat thickness, the first specific distance, and measurement sensitivity of a surface layer and measurement sensitivity of a deep layer when light is received at a position the first specific distance away from a light emitting means. A third specific distance and a fourth specific distance are computed corresponding to the computed fat thickness based on a predetermined relationship between the fat thickness, the third specific distance and a measurement sensitivity of an intervening layer and a measurement sensitivity of the deep layer when light is received at a position the third specific distance away from the light emitting means.

12 Claims, 14 Drawing Sheets

(51) Int. Cl.
*G01N 21/47* (2006.01)
*G01N 21/49* (2006.01)

(52) U.S. Cl.
CPC .......... *G01N21/4738* (2013.01); *G01N 21/49* (2013.01); *A61B 2562/0242* (2013.01); *G01N 2021/4742* (2013.01)

(56) References Cited

FOREIGN PATENT DOCUMENTS

JP 2010099414 A 5/2010
WO WO-2007139192 A1 12/2007

\* cited by examiner rectus abdominis
muscle diastasis

| TISSUE | ABSORPTION COEFFICIENT $\mu_a$ (mm$^{-1}$) | EQUIVALENT SCATTERING COEFFICIENT $\mu_s$ (mm$^{-1}$) |
|---|---|---|
| SKIN | 0.013 | 1.3 |
| FAT | 0.003 | 1.2 |
| MUSCLE | 0.02 | 0.6 |
| FAT (DEEP) | 0.003 | 1.2 |
| UTERUS | 0.02 | 0.6 |
| PLACENTA | 0.09 | 1.0 |
| FETUS | 0.01 | 2.0 |

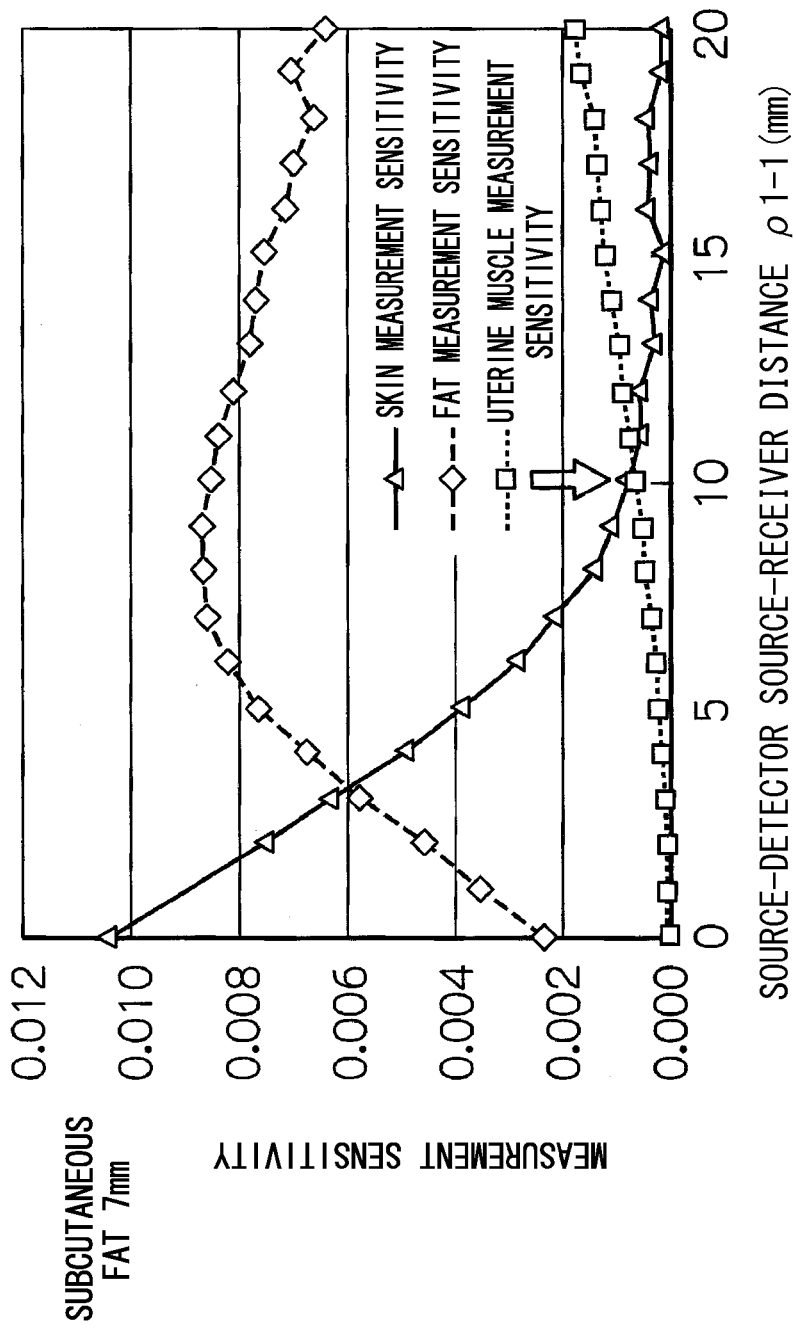

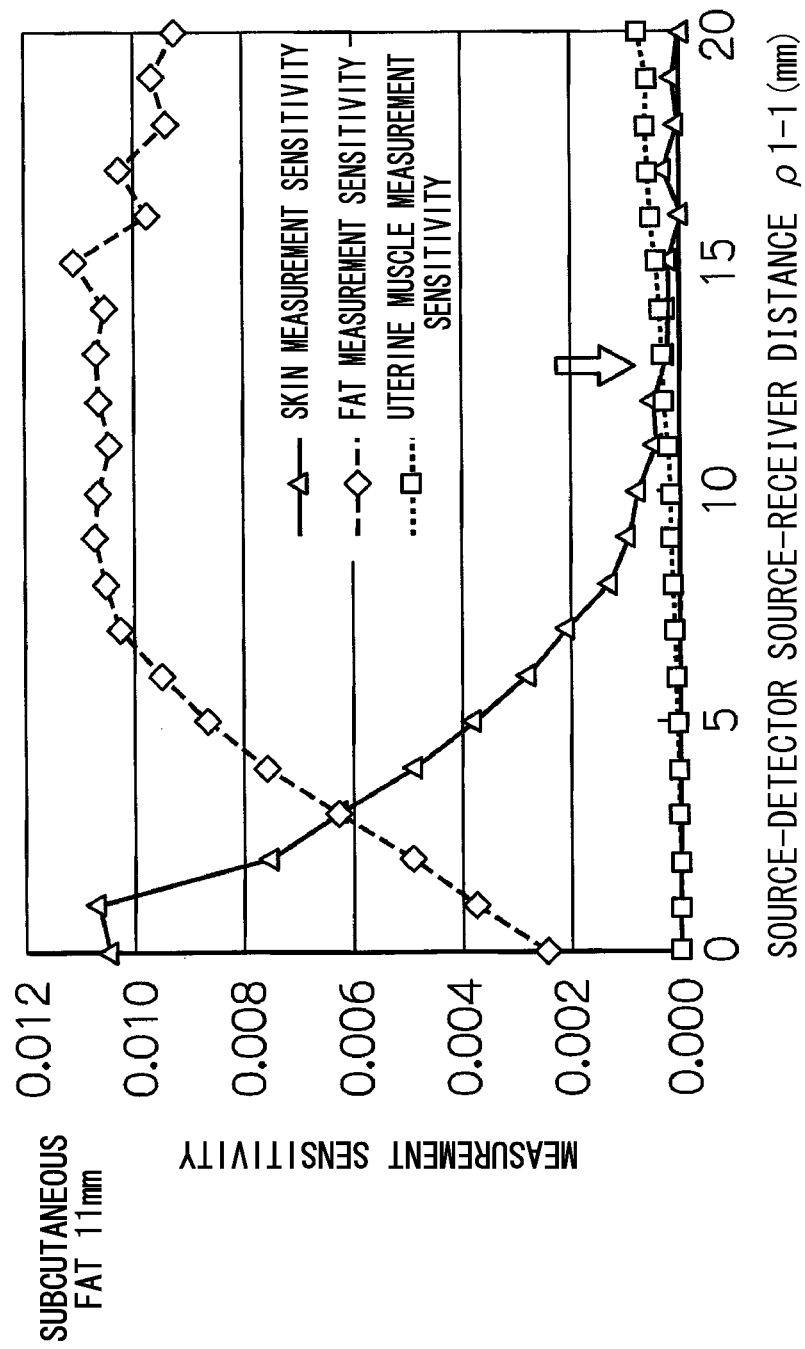

OPTICAL MEASURING DEVICE

TECHNICAL FIELD

The present invention relates to an optical measuring device, and in particular to an optical measuring device that measures the degree of light absorbance of deep layer tissue such as in a human body or a fruit.

BACKGROUND ART

There have already been attempts to measure light absorption coefficients of deep portions using spatial resolution by multi-point measurement, however multiple solutions arise, and a solution cannot be derived. To address this, there is a known method for a muscle and fat structure in which a relationship between a spatial slope S and a muscle absorption coefficient pa is expressed by introducing a second order function. The absorption coefficient of muscle is then determined by adding a means to input the thickness of fat, and using a computation formula corresponding to the thickness (Patent Document 1). Patent Document 1: Japanese Patent Application Laid-Open (JP-A) No. 2007-139191.

DISCLOSURE OF INVENTION

Technical Problem

For example, when measuring tissue at a deep site such as uterine muscle, there is skin, subcutaneous fat, rectus abdominis muscle or linea alba, and deep fat present between the uterine muscle and the body surface, and correction is required for the thickness and the absorption coefficient of the fat since there are large individual variation in these thicknesses. However, there is no specific method yet described to carry this out.

The present invention has been arrived at in the light of the above circumstances, and an object thereof is to obtain an optical measuring device that accurately measures light absorbance of deep layer tissue such as in a human body or a fruit.

Solution to Problem

In order to achieve the above objective, an optical measuring device of the present invention includes: a light emitting means that illuminates light onto a measurement target object formed from plural layers including a deep layer, and an intervening layer between a surface layer and the deep layer; a light reception means that receives light at a position a first specific distance away from the light emitting means such that out of the light emitted from the light emitting means is light received that has at least passed through the intervening layer, and that receives light at a different position from the first specific distance away position that out of the light emitted from the light emitting means has at least passed through the intervening layer, and that receives light at a position a second specific distance away from the light emitting means such that out of the light emitted from the light emitting means is light received that has at least passed through the intervening layer and the deep layer, and that receives light at a different position from the second specific distance away position that out of the light emitted from the light emitting means is light that has at least passed through the intervening layer and the deep layer; a spatial slope computation means that computes a first spatial slope based on light intensities of light respectively received at the first specific distance away position and at the different position from the first specific distance away position, and that computes a second spatial slope based on light intensities of light respectively received at the position the second specific distance away and at the different position from the second specific distance away position; and an absorption computation means that computes a light absorbance in the deep layer based on the computed first spatial slope, the computed second spatial slope, and a thickness of the intervening layer.

According to the optical measuring device of the present invention, light is illuminated by the light emitting means onto a measurement target object, light is received by the first light reception means at the position the first specific distance away from the light emitting means and light is received by the first light reception means at a different position from the first specific distance away position. Moreover, light is received by the second light reception means at the position the second specific distance away from the light emitting means and light is received by the second light reception means at the different position from the second specific distance away position.

Then the spatial slope computation means computes the first spatial slope based on light intensities of light respectively received at the first specific distance away position and at the different position from the first specific distance away position, and computes the second spatial slope based on light intensities of light respectively received at the position the second specific distance away and at the different position from the second specific distance away position. The absorption computation means then computes the light absorbance in the deep layer based on the computed first spatial slope, the computed second spatial slope, and the thickness of the intervening layer.

By thereby receiving light at the first specific distance away position and the different position from the first specific distance away position such that light received has passed through the intervening layer and computing the first spatial slope, and by receiving light at the second specific distance away position and the different position from the second specific distance away position such that light received has passed through the intervening layer and the deep layer and computing the second spatial slope, accurate measurement of the light absorbance of deep layer tissue such as that of a human body or a fruit by computing the light absorbance of the deep layer based on the thickness of the intervening layer.

The optical measuring device according to the present invention may be configured such that: the first specific distance is a distance corresponding to the intervening layer thickness derived based on a predetermined relationship between the intervening layer thickness, the first specific distance, and the measurement sensitivity of the surface layer and the measurement sensitivity of the deep layer when light from the light emitting means is received at the first specific distance away position; and the second specific distance is a distance corresponding to the intervening layer thickness derived based on a predetermined relationship between the intervening layer thickness, the second specific distance, and a measurement sensitivity of the intervening layer and a measurement sensitivity of the deep layer when light from the light emitting means is received at the second specific distance away position. The source-detector source-receiver distances that accurately measure the light absorbance of deep layer tissue, such as of a human body or a fruit, can accordingly be used.

An algorithm is required to appropriately set the source-detector source-receiver distance to correct for the thickness and absorption coefficient of fat, however a specific method to derive the appropriate source-detector source-receiver distance for measurement has not yet been described.

The optical measuring device according to the present invention may be configured to further include an acquisition means that acquires the intervening layer thickness. Moreover, the optical measuring device according to the present invention may be configured to further include: a first computation means that computes the first specific distance corresponding to the acquired intervening layer thickness based on a predetermined relationship between the intervening layer thickness, the first specific distance, and a measurement sensitivity of the surface layer and a measurement sensitivity of the deep layer when light from the light emitting means is received at the first specific distance away position; and a second computation means that computes the second specific distance corresponding to the acquired intervening layer thickness based on a predetermined relationship between the intervening layer thickness, the second specific distance, and a measurement sensitivity of the intervening layer and a measurement sensitivity of the deep layer when light from the light emitting means is received at the second specific distance away position.

Thus the first specific distance corresponding to the acquired intervening layer thickness is computed based on a relationship between the intervening layer thickness, the first specific distance, and a measurement sensitivity of the surface layer and a measurement sensitivity of the deep layer; and the second specific distance corresponding to the acquired intervening layer thickness is computed based on a relationship between the intervening layer thickness, the second specific distance, and a measurement sensitivity of the intervening layer and a measurement sensitivity of the deep layer. This thereby enables the source-detector source-receiver distances that accurately measure the light absorbance of the deep layer tissue, such as of the human body of a fruit, to be computed.

Configuration may be made such that the first computation means computes the first specific distance corresponding to the acquired intervening layer thickness based on the first specific distance predetermined for each of the intervening layer thickness where the measurement sensitivity of the surface layer and the measurement sensitivity of the deep layer match each other. Moreover, configuration may be made such that the first computation means computes the first specific distance corresponding to the acquired intervening layer thickness based on a relationship equation expressing a relationship between the intervening layer thickness and the first specific distance where the measurement sensitivity of the surface layer and the measurement sensitivity of the deep layer match each other.

Configuration may be made such that based on a relationship predetermined for each of the intervening layer thicknesses between the second specific distance and a coefficient of variance of a ratio of the measurement sensitivity of the intervening layer and a measurement sensitivity of the deep layer, the second computation means computes as the second specific distances a distance corresponding to a distance in the acquired intervening layer thickness where the coefficient of variance is at a minimum and a distance further away than the minimum. Moreover, configuration may be made such that the second computation means computes the second specific distance corresponding to the acquired intervening layer thickness based on a relationship equation expressing a relationship between the intervening layer thickness, and the distance corresponding to a distance where the coefficient of variance of the ratio of the measurement sensitivity of the intervening layer and the measurement sensitivity of the deep layer is at a minimum, and the distance further away than the minimum.

The optical measuring device including the acquisition means may be configured to further include: a storage means that is stored with computation parameters for computing light absorbance in the deep layer for each combination of light absorbance in the intervening layer and intervening layer thickness; wherein, the absorption computation means computes the light absorbance of the intervening layer based on the first spatial slope, reads the computation parameters corresponding to the acquired intervening layer thickness and the intervening layer light absorbance from the storage means, and computes the light absorbance in the deep layer based on the read computation parameters and the second spatial slope.

The acquisition means of the present invention may be configured to acquire a thickness of the intervening layer measured using an ultrasound imaging apparatus.

The acquisition means according to the present invention may be configured to compute the intervening layer thickness based on the first spatial slope and the second spatial slope that have been computed at four different distances respectively predetermined as the first specific distance, a distance to the different position from the first specific distance away position, the second specific distance, and a distance to the different position from the second specific distance away position.

The light reception means of the present invention may be configured to include plural light receptors that receive the light emitted by the light emitting means at plural positions that differ from each other in distance away from the light emitting means; from out of the plural light receptors, light is received by the light receptor selected to correspond to the first specific distance computed by the first computation means and light is received by the light receptor selected to correspond to the different position from the first specific distance away position; and from out of the plural light receptors, light is received by the light receptor selected to correspond to the second specific distance computed by the second computation means and light is received by the light receptor selected to correspond to the different position from the second specific distance away position.

The light emitting means of the present invention may be configured to include plural light illuminating portions that illuminate light onto the measurement target object, from out of the light illuminating portions, light is illuminated from the light illuminating portion selected to correspond to the first specific distance computed by the first computation means, and light is illuminated from the light illuminating portion selected to correspond to the different position from the first specific distance away position; and from out of the light radiating portions, light is illuminated from the light illuminating portion selected to correspond to the second specific distance computed by the second computation means, and light is illuminated from the light illuminating portion selected to correspond to the different position from the second specific distance away position.

The light emitting means of the present invention may be configured: to illuminate the measurement target object with light of each of two different wavelengths; such that the spatial slope computation means computes the first spatial slope and the second spatial slope for each of the two wavelengths; and the absorption computation means computes the light absorbance in the deep layer for each of two wavelengths, and based on the light absorbance in the deep layer for each of the two wavelengths, computes at a concentration of least one of oxygenated hemoglobin and/or deoxygenated hemoglobin.

The absorption computation means according to the present invention may be configured to compute the concentration of the oxygenated hemoglobin and the deoxygenated hemoglobin, and compute the oxygen saturation based on the computed concentrations of the oxygenated hemoglobin and the deoxygenated hemoglobin.

The above measurement target object may be a human body, configured such that the intervening layer includes skin and fat layer, and the deep layer includes a layer of uterine muscle.

The above measurement target object may be a fruit, configured such that the intervening layer includes a pericarb and flesh layer, and the deep layer includes a layer of seed chamber tissue.

Advantageous Effects of Invention

The optical measuring device according to the present invention has the advantageous effect of enabling the light absorbance of deep layer tissue such as that of a human body or a fruit to be accurately measured due to: receiving light at the first specific distance away position and at the different position from the first specific distance away position such that received light has passed through the intervening layer, computing a first spatial slope; and receiving light at the second specific distance away position and at the different position from the second specific distance away position such that received light has passed through the intervening layer and the deep layer, and computing a second spatial slope, then computing the light absorbance of the deep layer based on the intervening layer thickness.

BRIEF DESCRIPTION OF DRAWINGS

FIG. 10B is a graph of a relationship between measurement sensitivity and source-detector source-receiver distance when the subcutaneous fat thickness is 7 mm.

FIG. 10C is a graph of a relationship between measurement sensitivity and source-detector source-receiver distance when the subcutaneous fat thickness is 11 mm.

BEST MODE FOR CARRYING OUT THE INVENTION

Detailed explanation follows regarding exemplary embodiments of the present invention, with reference to the drawings.

In the first exemplary embodiment, explanation follows regarding of an example of a case in which a blood quantity, namely hemoglobin concentration and oxygen saturation, is measured in human uterine muscle tissue.

Figure 1:
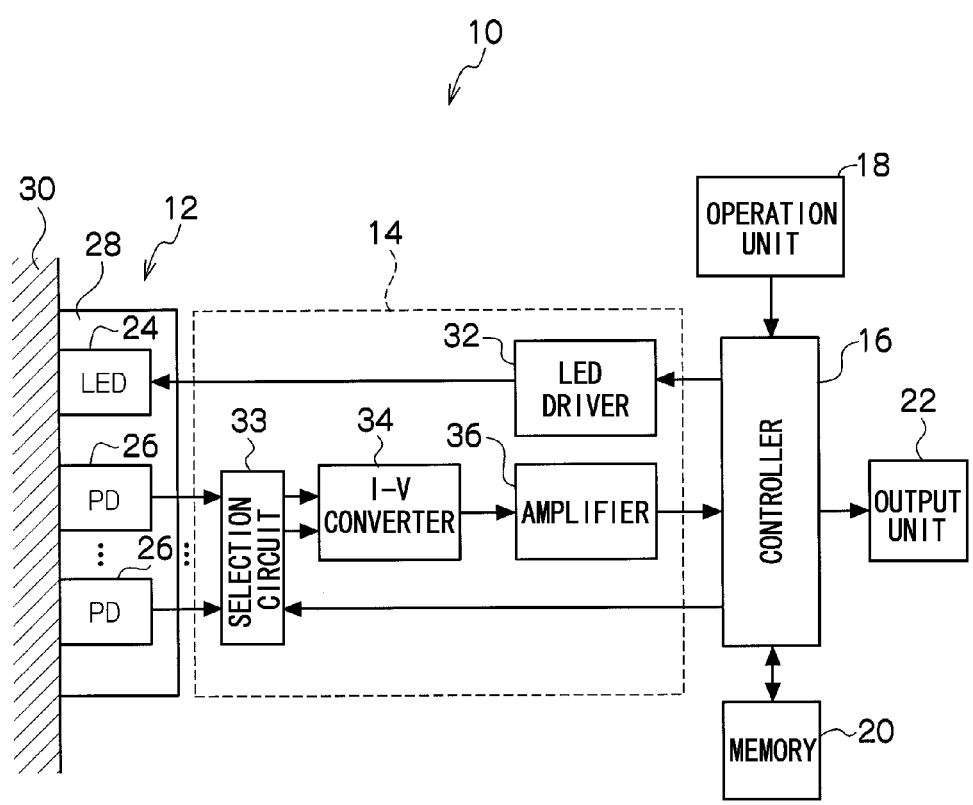
FIG. 1 is a schematic configuration diagram of an optical measuring device.

FIG. 1 shows a schematic configuration of an optical measuring device 10. As illustrated in FIG. 1, the optical measuring device 10 includes a probe 12, a driving device 14, a control unit 16, an operation unit 18, a memory 20, and an output unit 22.

The probe 12 is configured including a Light Emitting Diode (LED) 24 and plural Photodiodes (PDs) 26 provided for example inside a flexible planar member (such as a rubber member) 28. The probe 12 is brought into contact with an abdominal region 30 of a measurement subject in order to illuminate tissue of the uterine muscle of the measurement subject.

In the exemplary embodiment, as an example the LED 24 is a light emitting diode with two peak wavelengths, a first wavelength $\lambda 1$ and a second wavelength $\lambda 2$. The first wavelength $\lambda 1$ and the second wavelength $\lambda 2$ are set at wavelengths where the absorption by hemoglobin and water is low. Specifically, the wavelengths are set at two different wavelengths in a range of 700 nm to 900 nm. In the present exemplary embodiment, the first wavelength $\lambda 1$ is set at 770 nm, and the second wavelength $\lambda 2$ is set at 830 nm.

Placement is made such that the separation distance between the LED 24 and each of the PDs 26 are different from each other. The plural PDs 26 are for example disposed in a row at a specific separation. For example, the PDs 26 are placed such that the separation distance to the LED 24 is at every 3 mm over a range of 3 mm to 60 mm.

The driving device 14 includes a LED driver 32, a selection circuit 33, an I-V converter 34, and an amplifier 36.

In response to an instruction from the control unit 16, the LED driver 32 causes the LED 24 to emit light of a specific wavelength and a specific light intensity.

In response to an instruction from the control unit 16, the selection circuit 33 selects 4 of the PDs 26, and output from the 4 selected PDs 26 is output to the I-V converter 34.

The I-V converter 34 converts current obtained by photoelectric conversion of light received by the PDs 26 that have been selected by the selection circuit 33 into voltages, and outputs the voltages to the amplifier 36.

The amplifier 36 amplifies the voltage converted by the I-V converter 34 to a specific level, and the amplifier 36 outputs the amplified voltage as a signal indicating light intensity to the control unit 16.

The control unit 16 instructs the selection circuit 33 to select the four PDs 26, and instructs the LED driver 32 to cause the LED 24 to emit the light. The control unit 16 also computes hemoglobin concentration and the like by computation, described later, based on the light intensities received as a result by the selected four PDs 26. The computation result is output to the output unit 22. The output unit 22 is for example configured including a display or a printer, and the output unit 22 outputs by displaying or printing the computation result.

A measuring process routine program, described later, data used in such processing, and simulations results from previously executing such processing, are stored in advance in the memory 20.

Explanation next follows regarding a measurement method to measure the condition of uterine muscle.

Figure 2:
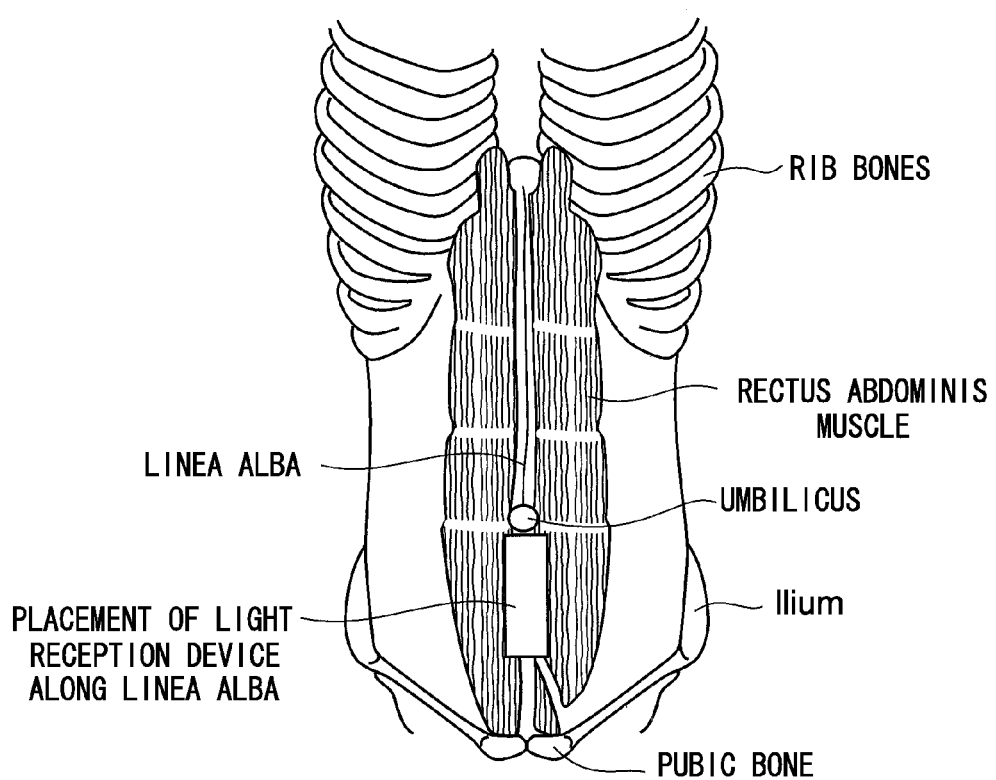
FIG. 2 is a diagram illustrating a situation in which a probe has been placed.
Figure 3:
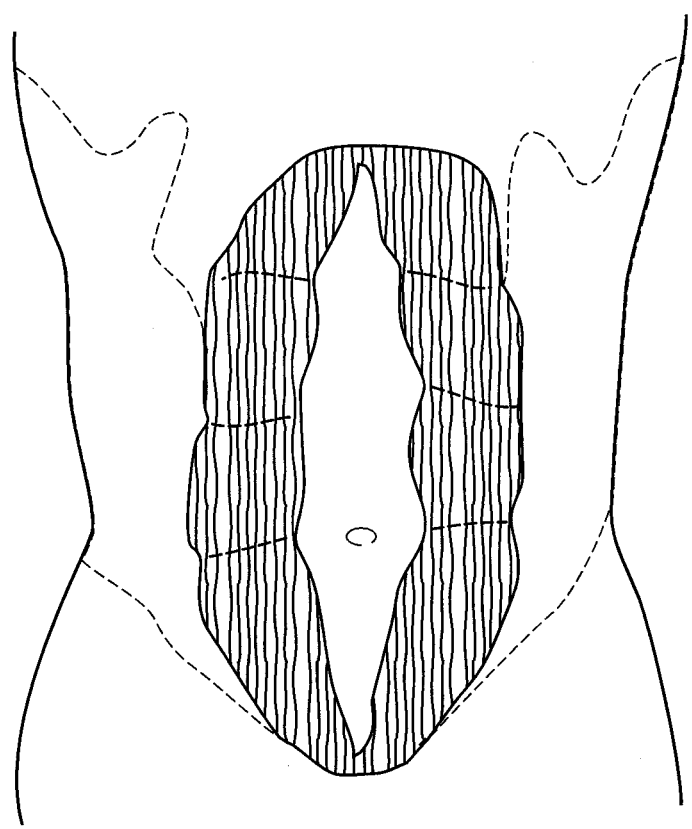
FIG. 3 is an illustration of rectus abdominis muscle diastasis.

First, as illustrated in FIG. 2, the probe 12 is placed below the umbilicus such that the PDs 26 are arrayed vertically. The influence of blood in the rectus abdominis muscles can accordingly be reduced. Moreover, there is less liability of influence from the rectus abdominis muscles when rectus abdominis muscle diastasis has occurred, as illustrated in FIG. 3.

Moreover, to obtain data of the optical characteristics of mainly fat, two of the PDs 26 are selected with short source-detector source-receiver distances corresponding to a specific distance ρ 1-1 and a specific distance ρ 1-2. Moreover, in order to obtain sufficient data of the uterine muscles, two of the PDs 26 are selected with long source-detector source-receiver distances corresponding to a specific distance ρ 2-1 and a specific distance ρ 2-2.

Figure 4:
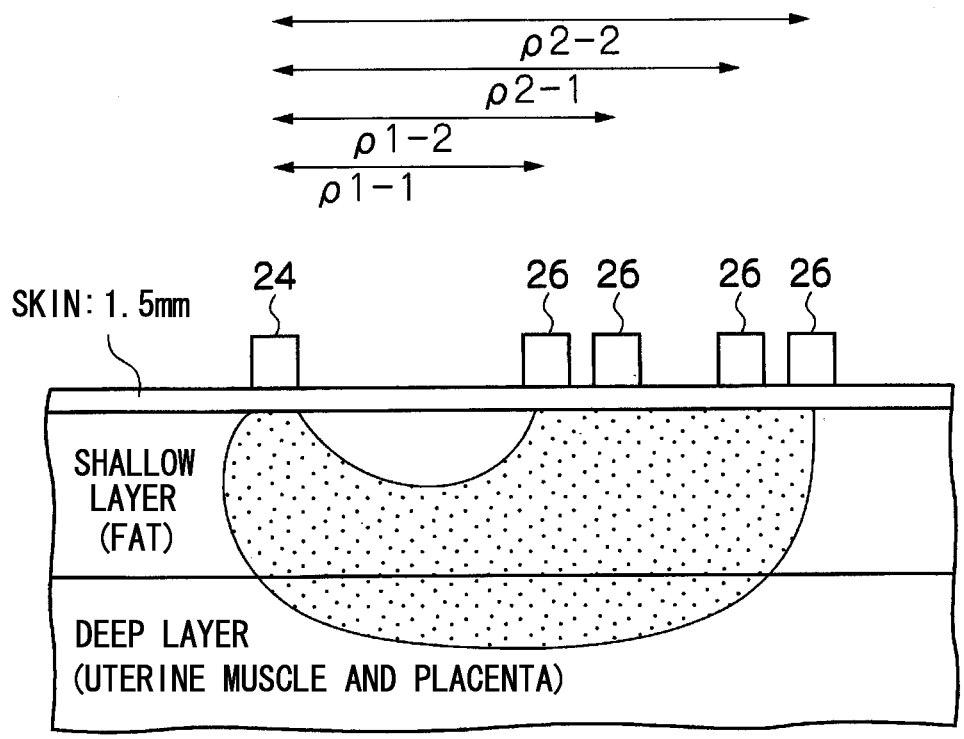
FIG. 4 is an explanatory image of source-detector source-receiver distance.

As illustrated in FIG. 4, the specific distance ρ 1-1 that is the distance between the LED and the PD 26 is set as a distance such that light emitted from the LED 24 arrives at the PD 26 after passing through layers that intervene to the far deep layers in a human abdominal region, namely through skin tissue (surface layers) and fat tissue (intermediate layer). The specific distance ρ 1-1 is computed by a method described later. As a result, in the present exemplary embodiment the specific distance ρ 1-1 is set as an example at 9 mm.

The specific distance ρ 1-2 that is the distance between the LED and the PD 26 is set at a distance different to the specific distance ρ 1-1 such that light emitted from the LED 24 arrives at the PD 26 after passes through the intervening layer of a human abdominal region. In the present exemplary embodiment, the specific distance ρ 1-2 is set as an example at ρ 1-1+3 mm.

The specific distance ρ 2-1 that is the distance between the LED and the PD 26 is set as a distance such that light emitted from the LED 24 arrives at the PD 26 after passing through the intervening layer of a human abdominal region and through the uterine muscle (deep layer). The specific distance ρ 2-1 is computed by a method described later. As a result, in the present exemplary embodiment, a third specific distance ρ 2-1 is set as an example at 25 mm.

A fourth specific distance ρ 2-2 that is the distance between the LED and the PD 26 is set as a different distance to the third specific distance ρ 2-1 such that light emitted from the LED 24 passes through the intervening layer of a human abdominal region and a region of deep layers to arrive at the PD 26. In the present exemplary embodiment the fourth specific distance ρ 2-2 is set as an example at the ρ 2-1+10 mm.

There are however large individual differences in the thickness of the tissue nearer to the surface than the uterine muscle, and so the thickness of fat is computed according to a method described later.

Then a spatial slope $S_{near}$ is computed according to following Equation (1) based on the received light intensities of the two PDs 26 corresponding to the source-detector source-receiver distances ρ 1-1, ρ 1-2, and a spatial slope $S_{far}$ is computed according to following Equation (2) based on the received light intensities of the two PDs 26 corresponding to the source-detector source-receiver distances ρ 2-1, ρ 2-1.

$$S_{near} = \ln\left(\frac{\text{received light intensity at } \rho_{1-1}}{\text{received light intensity at } \rho_{1-2}}\right) \quad (1)$$

$$S_{far} = \ln\left(\frac{\text{received light intensity at } \rho_{2-1}}{\text{received light intensity at } \rho_{2-2}}\right) \quad (2)$$

Based on the computed spatial slope $S_{near}$, a fat absorption coefficient $\mu_{af}$ is computed according to a relationship between the spatial slope $S_{near}$ and the fat absorption coefficient $\mu_{af}$ derived by theoretical analysis as described later.

Then computation parameters for a relationship equation between the spatial slope $S_{far}$ and a uterine muscle absorption coefficient $\mu_{au}$, derived by theoretical analysis as described later, that corresponds to the combination of computed thickness and computed fat absorption coefficient $\mu_{af}$ are read from a database. Then based on the computed spatial slope $S_{far}$, the read computation parameters are then employed to compute the uterine muscle absorption coefficient $\mu_{au}$ according to the relationship equation between the spatial slope $S_{far}$ and the uterine muscle absorption coefficient $\mu_{au}$.

Explanation next follows regarding the theoretical analysis.

Figure 5:
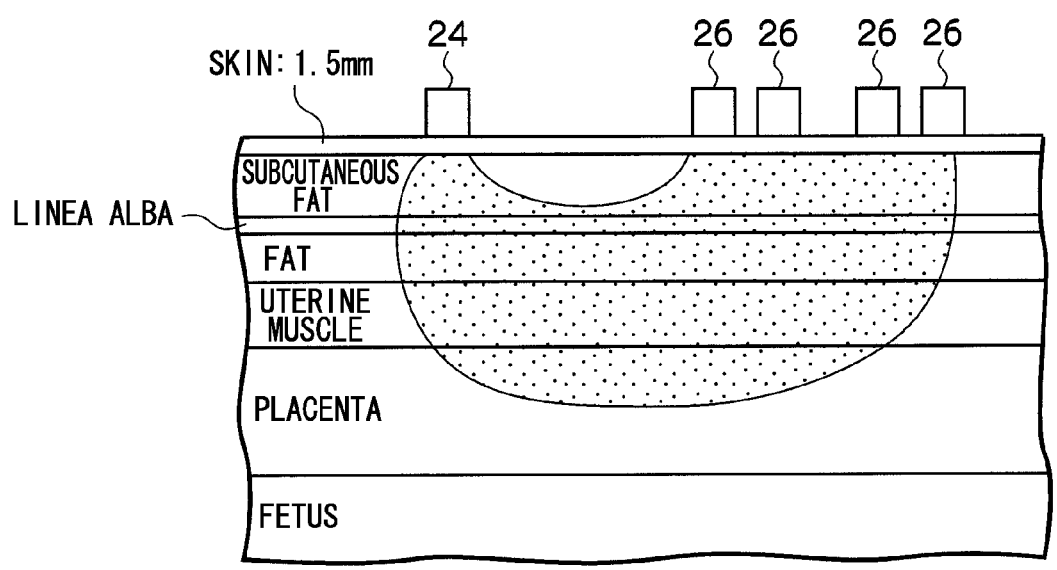
FIG. 5 is an explanatory diagram of a 7 layer model.
Figures 6, 7:
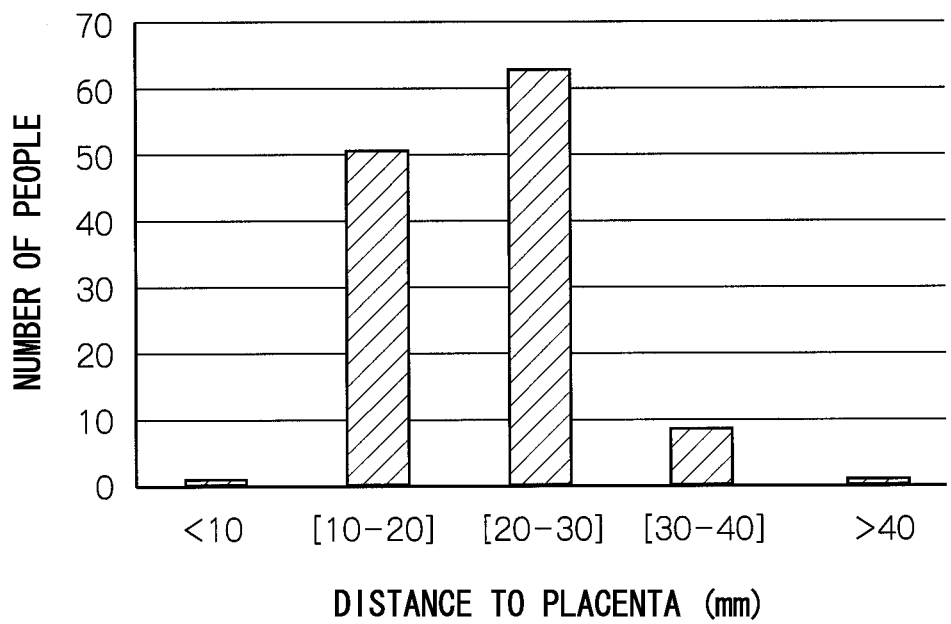
FIG. 6 is a graph illustrating data of distances to the placenta.
FIG. 7 is a table illustrating absorption coefficients and equivalent scattering constants for each of the layers.

First, a living tissue model is made, and light propagation analysis is performed by Monte Carlo simulation using a 7-layer model, as illustrated in FIG. 5, of skin/subcutaneous fat/linea alba/fat/uterine muscle/placenta/fetus to investigate the light path length through each tissue. As an algorithm for light propagation a generally employed algorithm may be employed in which photon groups are set on random walks through the model, and the intensity of photon groups is attenuated according to the type of medium through which they are passing. As illustrated in FIG. 6, analysis is performed whilst changing the thickness of the subcutaneous fat based on data of distance to the placenta. Note that the optical constants of each of the layers are set as illustrated in FIG. 7 and the number of individual photons is $10^8$ photons.

Figure 8:
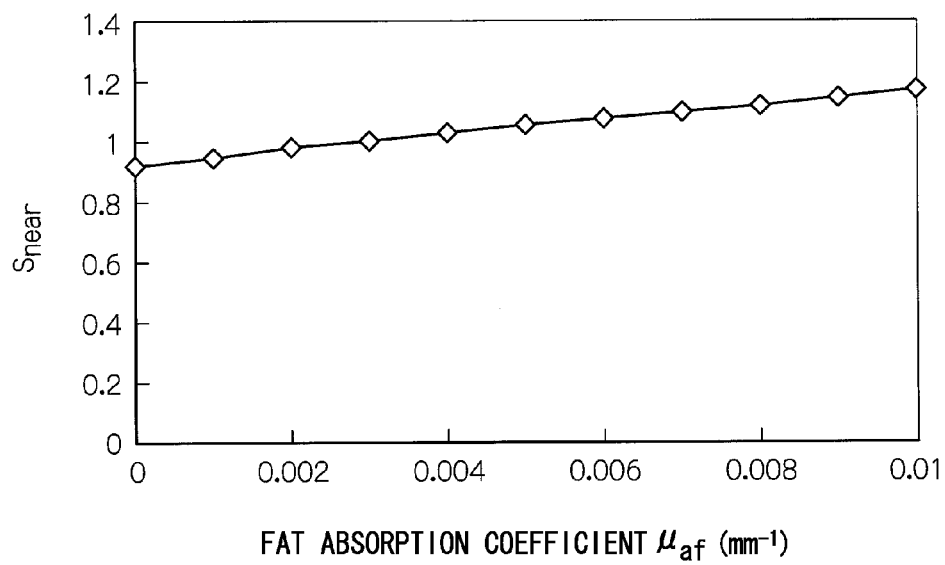
FIG. 8 is a graph illustrating a relationship between an absorption coefficient of fat and spatial slope $S_{near}$.

Performing the theoretical analysis as described above derives the combination of spatial slope $S_{near}$ and fat absorption coefficient $\mu_{af}$, and derives the relationship equation between the spatial slope $S_{near}$ and the fat absorption coefficient $\mu_{af}$ from an $S_{near}$–$\mu_{af}$ curve representing a relationship between the spatial slope $S_{near}$ and the fat absorption coefficient $\mu_{af}$ as illustrated in FIG. 8. The $S_{near}$–$\mu_{af}$ curve can be approximated to a quadratic equation in relation to the spatial slope $S_{near}$ as illustrated in following Equation (3).

$$\mu_{af} = aS_{near}^2 + bS_{near} + c \quad (3)$$

Wherein a, b, c are parameters, and these parameters are derived for each wavelength from results of Monte Carlo simulation as illustrated in FIG. 8, and stored in advance in the memory 20. The absorption coefficient $\mu_{af}$ can be derived thereby as long as the spatial slope $S_{near}$ is known.

Note that in the example described above in FIG. 8, the spatial slope $S_{near}$ is computed from the received light intensity when the shorter source-detector source-receiver distances ρ 1-1, ρ 1-2 are 9 mm and 12 mm, with the subcutaneous fat thickness at 7 mm and the uterine muscle absorption coefficient at 0.02 mm$^{-1}$. Since the difference of the spatial slope $S_{near}$ due to the thickness of the skin is small, only one type of parameters of the relationship equation between the spatial slope $S_{near}$ and the fat absorption coefficient $\mu_{af}$ is derived irrespective of the thickness of the skin.

Figure 9:
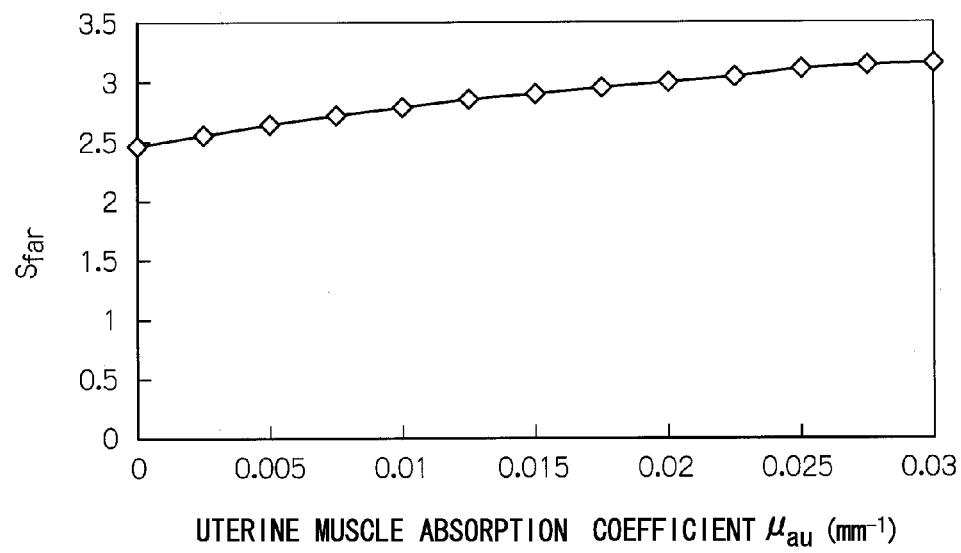
FIG. 9 is a graph illustrating a relationship between an absorption coefficient of uterine muscle and spatial slope $S_{far}$.

Moreover, a $S_{far}$-$\mu_{au}$ curve representing the relationship between the spatial slope $S_{far}$ and the uterine muscle absorption coefficient $\mu_{au}$ is derived for each of the combinations of subcutaneous fat thickness and fat absorption coefficient. An $S_{far}$-$\mu_{au}$ curve such as illustrated in FIG. 9 is formularized for each of the combinations of the subcutaneous fat thickness and the fat absorption coefficient, and stored in the memory 20. For example, a $S_{far}$-$\mu_{au}$ curve can be approximated to a quadratic equation in relation to spatial slope $S_{far}$, and parameters of the approximated quadratic equation then derived for each wavelength and for each combination of subcutaneous fat thickness and fat absorption coefficient. These are then stored in advance in the memory 20.

Note that in the example in FIG. 9, the spatial slope $S_{far}$ is computed from the received light intensity when the longer source-detector source-receiver distances ρ 2-1, ρ 2-2 are 25 mm and 35 mm, with the subcutaneous fat thickness at 7 mm and the fat absorption coefficient at 0.003 mm$^{-1}$.

The fat absorption coefficient and the uterine muscle absorption coefficient are computed based on the parameters of the relationship equation obtained as a result of the above theoretical analysis. The fat absorption coefficient and the uterine muscle absorption coefficient here are computed based on the received light intensities of the PDs 26 when the LED 24 emits the first wavelength λ1, and computed based on the received light intensities of the PDs 26 when the LED 24 emits the second wavelength λ2.

The oxygenated hemoglobin concentration (mM) of the uterine muscles is computed according to the following Equation (4).

$$[HbO_2] = \frac{\varepsilon^{\lambda 2}_{Hb}\mu^{\lambda 1}_{au} - \varepsilon^{\lambda 1}_{Hb}\mu^{\lambda 2}_{au}}{\varepsilon^{\lambda 1}_{HbO_2}\mu^{\lambda 2}_{Hb} - \varepsilon^{\lambda 2}_{HbO_2}\mu^{\lambda 1}_{Hb}} \quad (4)$$

Moreover, the deoxygenated hemoglobin concentration (mM) of the uterine muscle is computed according to the following Equation (5).

$$[Hb] = \frac{\varepsilon^{\lambda 1}_{Hb}\mu^{\lambda 2}_{au} - \varepsilon^{\lambda 2}_{Hb}\mu^{\lambda 1}_{au}}{\varepsilon^{\lambda 1}_{HbO_2}\mu^{\lambda 2}_{Hb} - \varepsilon^{\lambda 2}_{HbO_2}\mu^{\lambda 1}_{Hb}} \quad (5)$$

The oxygen saturation (%) of the uterine muscles is computed according to the following Equation (6).

$$S_uO_2 = \frac{[HbO_2]}{[HbO_2]+[Hb]} \times 100(\%) \quad (6)$$

Wherein λ1 is 830 mm, λ2 is 770 mm. $\varepsilon^{\lambda 1}_{Hb}$ is the molecular absorption coefficient of deoxygenated hemoglobin at first wavelength λ1, $\varepsilon^{\lambda 2}_{Hb}$ is the molecular absorption coefficient of deoxygenated hemoglobin at second wavelength λ2, $\varepsilon^{\lambda 1}_{Hb02}$ is the molecular absorption coefficient of oxygenated hemoglobin at first wavelength λ1, and $\varepsilon^{\lambda 2}_{Hb02}$ is the molecular absorption coefficient of oxygenated hemoglobin at second wavelength λ2, and known values are employed for each of these. The $\mu^{\lambda 1}_{au}$ is the absorption coefficient of the uterine muscles at first wavelength λ1, the $\mu^{\lambda 2}_{au}$ is the absorption coefficient of the uterine muscles at second wavelength λ2.

Explanation now follows regarding a computation method of the source-detector source-receiver distances ρ 1-1 to ρ 2-2.

First explanation follows regarding a method of computing the short source-detector source-receiver distances ρ 1-1, ρ 1-2 to measure the optical characteristics of fat.

In order to determine the optical characteristics of fat, it is necessary to assume that there is little susceptibility to influence from changes in skin, there is great susceptibility to measurement sensitivity of fat, and there is little susceptibility to influence from changes in uterine muscles. Thus in the present exemplary embodiment, the source-detector source-receiver distances are computed for the source-detector source-receiver distances ρ 1-1, ρ 1-2 so as to lessen the measurement sensitivity of skin and uterine muscles.

Figure 10A:
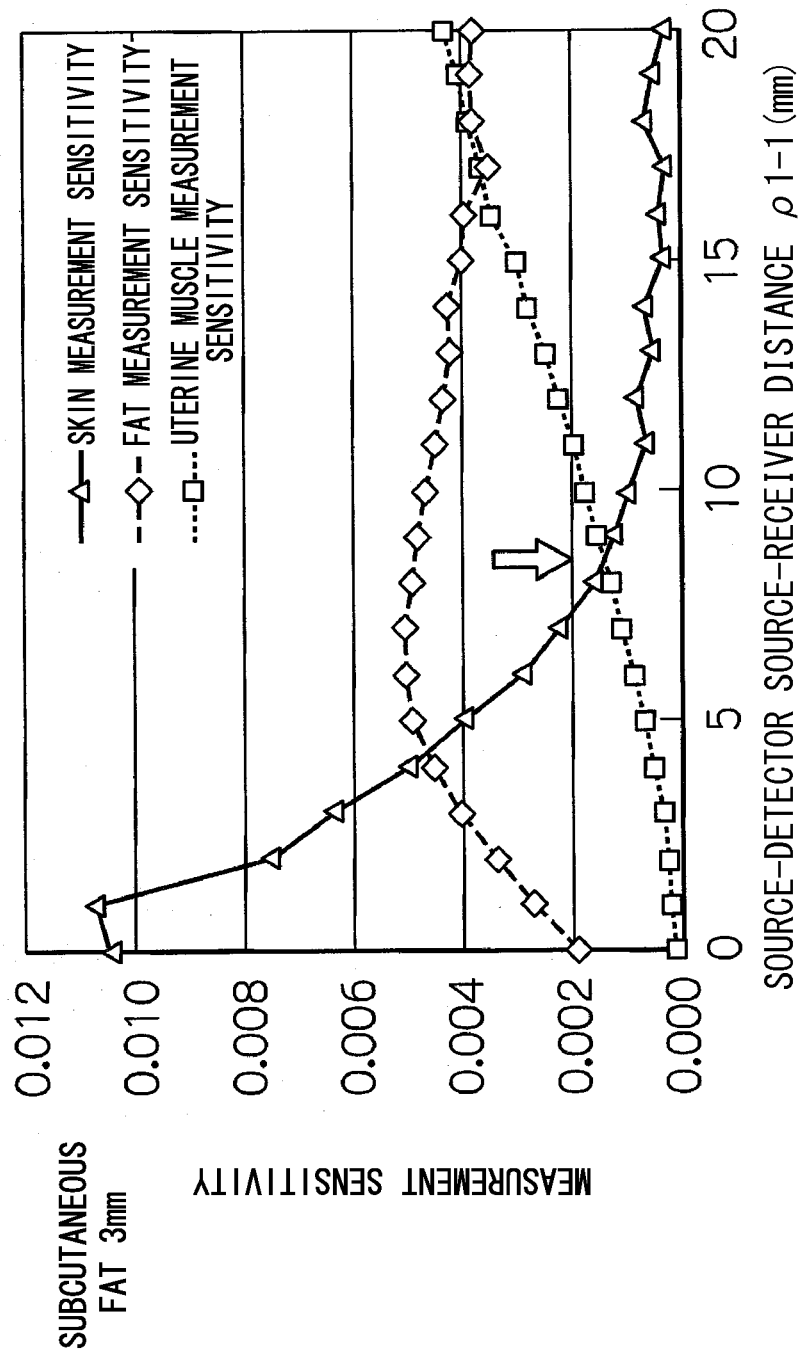
FIG. 10A is a graph of a relationship between measurement sensitivity and source-detector source-receiver distance when the subcutaneous fat thickness is 3 mm.

For example, for each of the plural thicknesses of subcutaneous fat, the measurement sensitivity of skin, the measurement sensitivity of fat and the measurement sensitivity of uterine muscles are computed while changing the source-detector source-receiver distance ρ 1 and changing the source-detector source-receiver distance ρ 1-2 (=ρ 1-1+3), and the relationship between each of the measurement sensitivities and the source-detector source-receiver distance ρ 1-1 is derived for each of the thicknesses of the subcutaneous fat, as illustrated in FIG. 10A to FIG. 10C.

The measurement sensitivity here is the change amount of light intensity when the tissue absorption coefficient is changed by 1%. The change amount of light intensity is the logarithm of the ratio of before-change received light intensity I1 and post-change received light intensity I2, namely log(I1/I2). For example, the measurement sensitivity of skin in the source-detector source-receiver distance ρ 1-1 is the increase in light absorbance on the source-detector source-receiver distance ρ 1-1 when the skin absorption coefficient is increased by 1%.

In the example of FIG. 10A to FIG. 10C above, with the source-detector source-receiver distance ρ 1-2 set as ρ 1-1+3 mm (3 mm is set in consideration of the physical size of the light receptor), the skin thickness is 1.5 mm, and the various thicknesses of subcutaneous fat are from 1 to 20 mm. The thickness of the linea alba is taken as 3 mm, the thickness of the deep fat is taken at 3 mm, and the thickness of the uterine muscle is taken at 5 mm.

As illustrated in FIG. 10A to FIG. 10B, the relationship between the skin measurement sensitivity and the source-detector source-receiver distance ρ 1-1 slopes down to the right hand side, and the relationship between the uterine muscles measurement sensitivity and the source-detector source-receiver distance ρ 1-1 slopes up to the right hand side. Consequently, as a source-detector source-receiver distance that makes the measurement sensitivities of the skin and the uterine muscles both small, the optimum source-detector source-receiver distance can be considered to be the intersection of both (see the arrow indications in FIG. 10A to FIG. 10O) (the point where the measurement sensitivities of both match each other), and the optimum source-detector source-receiver distance ρ 1 is derived for each of the fat thicknesses.

If t(mm) denotes the thickness of an intervening layer between the body surface and the uterine muscles, then within a range of t up to 14 mm the optimum source-detector source-receiver distance y(mm) changes linearly, and y is constant at 15 mm for 15 mm and above. An equation for deriving y in a range of t of 14 mm or less is expressed by the following Equation (7).

$$y=0.63t+6.13 \qquad \text{Equation (7)}$$

Above Equation (7) expresses a relationship between the thickness of the intervening layer and the source-detector source-receiver distance where the measurement sensitivities of the skin and uterine muscles match.

As described above, based on the fat thickness, the short distance source-detector source-receiver distance ρ 1 is computed according to Equation (7), and the ρ 1-2 is computed by adding a fixed distance based on the physical size of the light receptor (for example 3 mm) to the ρ 1-1.

Explanation next follows regarding a computation method of the long distance source-detector source-receiver distances ρ 2-1, ρ 2-2 employed for measuring the uterine muscle optical characteristics.

In order to determine the optical characteristics of the uterine muscles, it is necessary to assume that there is little susceptibility to influence from changes in the skin (in the present exemplary embodiment there is no particular consideration given to this factor since it is known from the present analysis that there is hardly any influence from the skin to the spatial slope of distant regions), there is great susceptibility to measurement sensitivity of the uterine muscles, and since there is noise in electrical circuits, there is a need to obtain a large received light intensity to improve the S/N ratio.

The measurement sensitivity of fat does not reduce by much at sites far away from the LED 24, and so an index is taken of a ratio of the measurement sensitivities of uterine muscles and fat. This is denoted $R_{u\text{-}f}$.

Figure 11A:
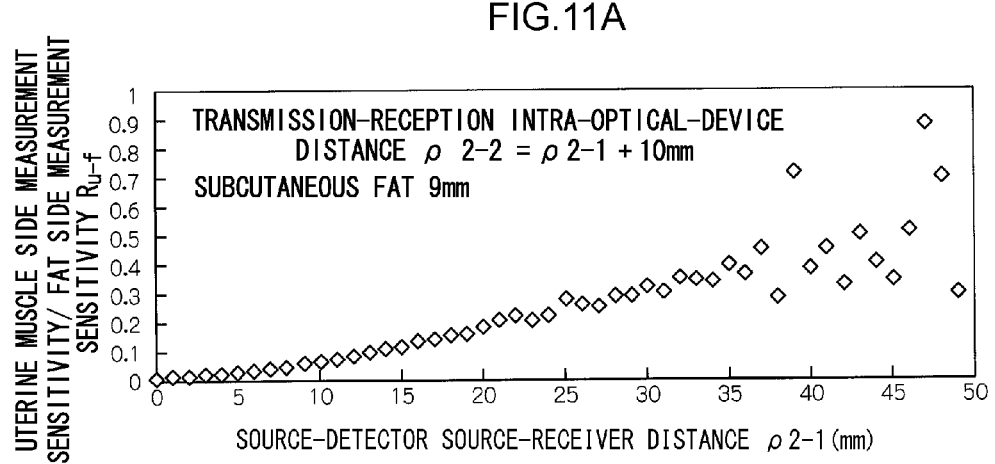
FIG. 11A is a graph indicating a relationship of source-detector source-receiver distance and a ratio of measurement sensitivities.

When the relationship between the measurement sensitivity ratio $R_{u\text{-}f}$ and the source-detector source-receiver distance ρ 2-1 is derived it rises towards the right hand side, as illustrated in FIG. 11A, and however the variance gradually increases as the source-detector source-receiver distance ρ 2-1 increases, and the increasing trend of the measurement sensitivity ratio $R_{u\text{-}f}$ becomes smaller.

The region where the variance in the theoretical calculation becomes larger indicates that event probability is low, and is therefore important reference data indicating that the S/N ratio is anticipated to deteriorate in actual measurements.

Figure 11B:
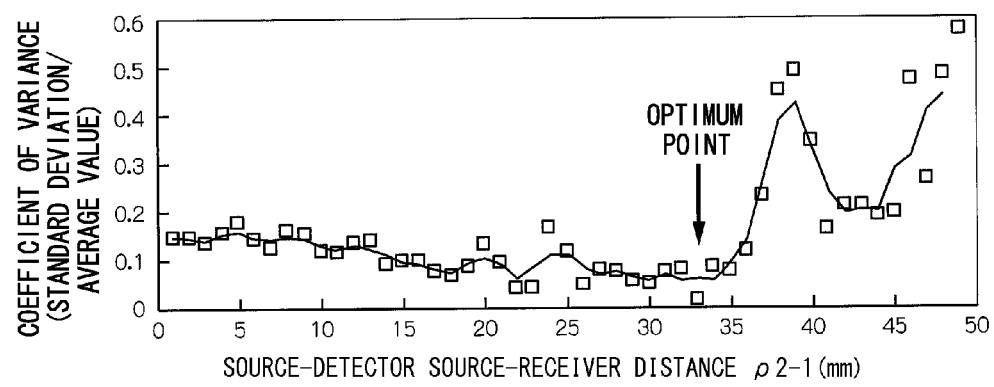
FIG. 11B is a graph illustrating a relationship between source-detector source-receiver distance and coefficient of variance of a ratio of measurement sensitivities.

By giving evaluation values to the magnitude of variance with respect to the magnitude of the $R_{u\text{-}f}$, a source-detector source-receiver distance ρ 2-1 can be sought that gives a large uterine muscles measurement sensitivity and also a small variance. When data is acquired by performing AD conversion at about 100 kHz, the energy illuminated during 1 sampling period is $1 \times 10^{-8}$ J (for a 1 mW LED), with the number of individual photons of wavelength 770 nm being $4 \times 10^{10}$ photons. In the analysis program, a symmetrical flat plane perpendicularly to the illumination optical axis is employed, and the light reception efficiency is several tens of times, and so a variance close to that obtained in actual measurements is obtained with the analysis program executed with a number of photons that is of the order of $10^8$. The determination result of the coefficient of variance (=standard deviation/average value) for the 3 sets of data in the graph illustrated in FIG. 11A is illustrated in the graph of FIG. 11B, and shows clearly that there is a point where the coefficient of variance becomes small.

The source-detector source-receiver distance needs to be long to make the measurement sensitivity ratio $R_{u\text{-}f}$ large, as illustrated in FIG. 11A. A source-detector source-receiver distance with good S/N ratio is obtained by finding a point where the coefficient of variance of the $R_{u\text{-}f}$ is as small as possible. The relationship in FIG. 11A rises to the right hand side, and the relationship in FIG. 11B is a U-shaped curve. Therefore, within a distance corresponding to the source-detector source-receiver distance with a minimum coefficient of variance of the $R_{u\text{-}f}$ (the bottom portion of the U-shape), the long source-detector source-receiver distance is considered to be an optimum source-detector source-receiver distance ρ 2-1, where the uterine muscles measurement sensitivity is large and the variance is small (see the arrow in FIG. 11B). The optimum source-detector source-receiver distance P is derived accordingly for each of the fat thicknesses.

When the thickness of the intervening layer from the body surface to the uterine muscles is t (mm), since t varies linearly within a range to 40 mm, the optimum source-detector source-receiver distance y (mm) in a range of t of 40 mm or less is represented by the following Equation (8) for deriving y.

$$y=0.30t+31.8 \qquad \text{Equation (8)}$$

Above Equation (8) expresses a relationship between the thickness of the intervening layer, and the long source-detector source-receiver distance that is the distance corresponding to the source-detector source-receiver distance where the coefficient of variance of the $R_{u\text{-}f}$ is a minimum.

The short distance source-detector source-receiver distance ρ 2-1 is computed based on the fat thickness as described above according to Equation (8), and the ρ 2-2 is computed by adding a fixed distance based on the physical size of the light receptor (for example 3 mm) to the ρ 2-1.

Explanation next follows regarding a method for computing the fat thickness from the distribution of received light intensity.

As an example of a source-detector source-receiver distance capable of efficiently detecting the thickness of shallow layers, we now consider a case in which there is a spatial slope $S_{4,5\text{-}6,5}$ based on the light intensity when ρ 1-1=4.5 mm, ρ 1-2=6.5 mm, and there is a spatial slope $S_{30\text{-}40}$ based on the light intensity when ρ 2-1=30 mm, ρ 2-2=40 mm.

Figure 12A:
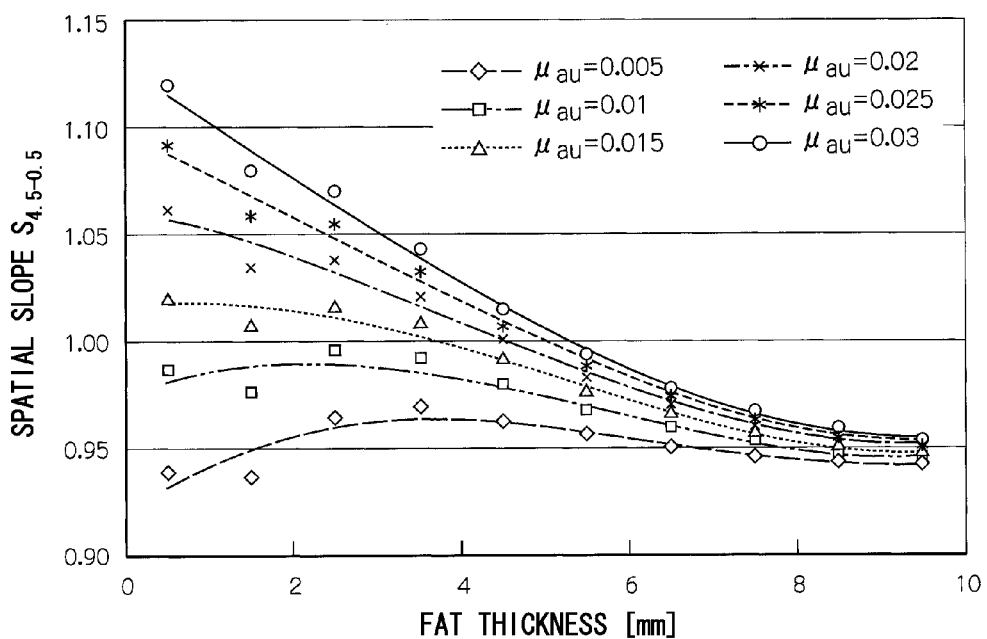
FIG. 12A is a graph illustrating a relationship between fat thickness and spatial slope for each uterine muscle absorption coefficient.
Figure 12B:
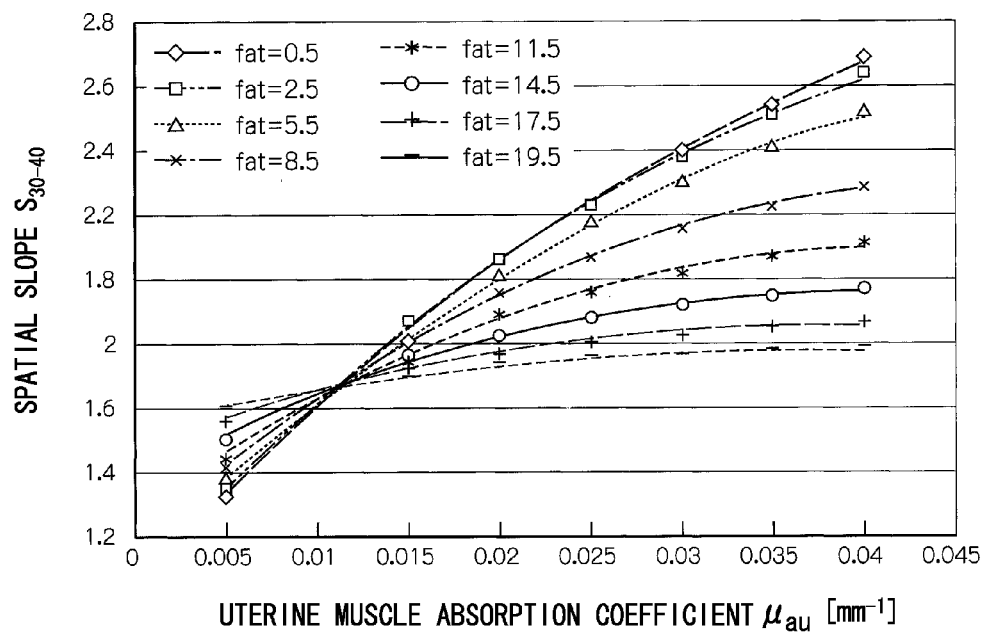
FIG. 12B is a graph illustrating a relationship between uterine muscle absorption coefficient and spatial slope for each fat thickness.

FIG. 12A and FIG. 12B are two diagrams of a result of investigation by theoretical analysis into the influence exerted by the fat thickness and the absorption coefficient of the uterine muscle for $S_{4,5\text{-}6,5}$ and $S_{30\text{-}40}$.

Formulizations of the groups of curves of FIG. 12A and FIG. 12B are given in the following 2 equations. h is the fat layer thickness (mm), and $\mu_{au}$ is the uterine muscle absorption coefficient $(mm^{-1})$.

$$S_{4,5\text{-}6,5}=(A_1\mu_{au}^3+A_2\mu_{au}^2+A_3\mu_{au}+A_4)h^3+(A_5\mu_{au}+A_6)h^2+(A_7\mu_{au}+A_8)h+(A_9+A_{10})$$

$$S_{30\text{-}40}=(B_1h^2+B_2h+B_3)^2+(h+)\mu_{au}+(B_6h+B_7)$$

Examples of each of the constants are as set out below.

$A_1$=−66.7, $A_2$=3.43, $A_3$=−0.056, $A_4$=0.0005, $A_5$=0.194, $A_6$=−0.0061, $A_7$=−2.04, $A_8$=0.035, $A_9$=7.67, $A_{10}$=0.902, $B_1$=2.28, $B_2$=−30.1, $B_3$=−448.4, $B_4$=−2.53, $B_5$=66.2, $B_6$=0.026, $B_7$=1.01

Solving the above non-linear simultaneous equations by numerical computation enables the two unknown constants h, $\mu_{au}$ to be derived from the two spatial slope $S_{4,5\text{-}6,5}$ and $S_{30\text{-}40}$. Since sensor placement is made with priority consideration given to deriving the fat thickness for these measurements, they are not always the optimum conditions for deriving information about deep tissue such as the uterine muscles. Thus use is only made here to solve the fat thickness h, and the value of $\mu_{au}$ is obtained with high precision by computation using the method described above set with the optimum source-detector source-receiver distance.

Figure 13:
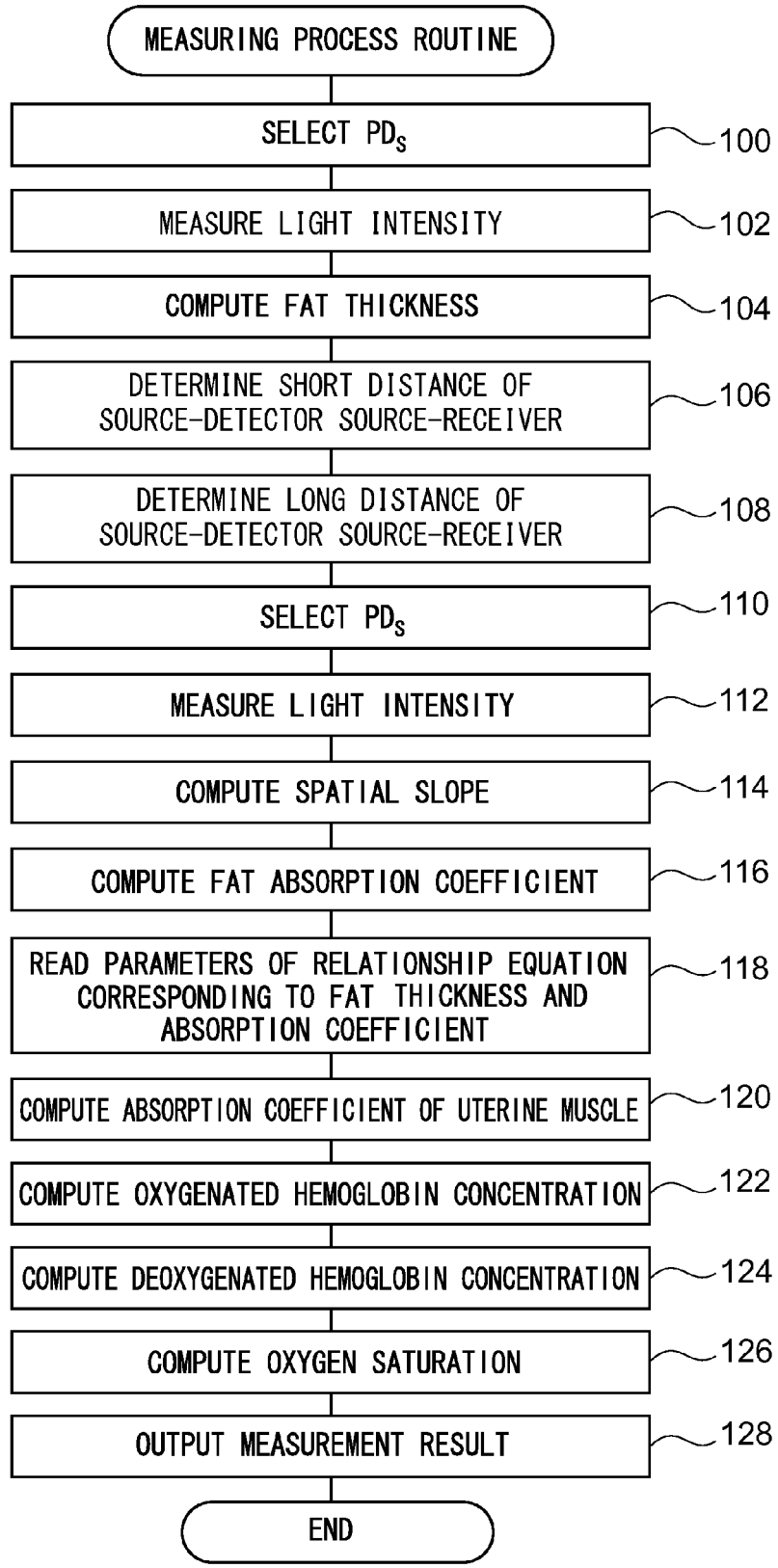
FIG. 13 is a flow chart illustrating content of a measuring process routine in an optical measuring device.

Explanation next follows regarding operation of the present exemplary embodiment, with the measuring processing executed by the control unit 16 explained with reference to the measuring process routine illustrated in FIG. 13. Note that this processing is executed with the power of the optical measuring device 10 switched ON.

When performing measurements, the probe 12 is placed in contact with the measurement subject, and an instruction is given to the start measuring by operating the operation unit 18.

At step 100, four predetermined PDs 26 are selected at the light reception positions corresponding to the source-detector source-receiver distances ρ 1-1, ρ 1-2, ρ 2-1, ρ 2-2 that are capable of efficiently detecting the fat thickness. Then at step 102, an instruction it given to the LED driver 32 to emit light from the LED 24, and the light intensity of the light received by the four PDs 26 selected at step 100 is acquired from the amplifier 36.

Then at step 104 the measurement subject fat thickness is computed based on the light intensity of light received by the four PDs 26 acquired at step 102.

At the next step 106, based on the fat thickness computed at step 104, the short source-detector source-receiver distance ρ 1-1 is computed according to Equation (7), and the ρ 1-2 is computed. Then, at step 108, based on the fat thickness computed at step 104, the long source-detector source-receiver distance ρ 2-1 is computed according to Equation (8), and the ρ 2-2 is computed.

At the next step 110, two PDs 26 are selected at light reception positions corresponding to the source-detector source-receiver distance ρ 1-1, ρ 1-2 computed at step 106, and two PDs 26 are selected at light reception positions corresponding to the source-detector source-receiver distance ρ 2-1, ρ 2-2 computed at step 108.

Then at step 112, the LED driver 32 is instructed to emit light from the LED 24, and the light intensity of light received by the four PDs 26 selected at step 110 is acquired from the amplifier 36. Note that light is emitted in the sequence of the first wavelength λ1 then the second wavelength λ2, and the respective light intensities thereof acquired.

At step 114, based on the light intensities of the first wavelength λ1 and the second wavelength λ2 measured at step 112, the spatial slope $S_{near}$ of the first wavelength λ1 and the second wavelength λ2 are computed according to Equation (1), and then the spatial slope $S_{far}$ of the first wavelength λ1 and the second wavelength λ2 are computed according to Equation (2).

Then at step 116, the parameters for the relationship equation between the spatial slope $S_{near}$ and the fat absorption coefficient $\mu_{af}$ are read from the memory 20, and then based on the spatial slope $S_{near}$ of the first wavelength λ1 and the second wavelength λ2 derived at step 114, the fat absorption coefficient $\mu^{\lambda 1}{}_{af}$, $\mu^{\lambda 2}{}_{af}$ for the first wavelength λ1 and the second wavelength λ2 are computed according to the relationship equation between the spatial slope $S_{near}$ and the fat absorption coefficient $\mu_{af}$.

In the next step 118, the parameters of the relationship equation between the spatial slope $S_{far}$ and the uterine muscle absorption coefficient $\mu_{au}$, corresponding to the combination of the fat thickness computed at step 104 and the fat absorption coefficient $\mu^{\lambda 1}{}_{af}$, $\mu^{\lambda 2}{}_{af}$ of the first wavelength λ1 and the second wavelength λ2 computed at step 116, are read from the memory 20.

Then at step 120, based on the spatial slope $S_{far}$ of the first wavelength λ1 and the second wavelength λ2 derived at step 114, the parameters read at step 118 are used to compute the uterine muscles absorption coefficient $\mu^{\lambda 1}{}_{au}$, $\mu^{\lambda 2}{}_{au}$ of or the first wavelength λ1 and the second wavelength λ2 according to the relationship equation between the spatial slope $S_{far}$ and the uterine muscle absorption coefficient $\mu_{au}$.

Then at step 122, based on the uterine muscles absorption coefficient $\mu^{\lambda 1}{}_{au}$, $\mu^{\lambda 2}{}_{au}$ derived at step 120, the oxygenated hemoglobin concentration [HbO$_2$] is derived according to Equation (4).

At step 124, the deoxygenated hemoglobin concentration [Hb] is derived according to Equation (5) based on the uterine muscles absorption coefficient $\mu^{\lambda 1}{}_{au}$, $\mu^{\lambda 2}{}_{au}$ derived at step 120. Then at step 126, the oxygen saturation $S_tO_2$ is computed according to Equation (6) based on the oxygenated hemoglobin concentration [HbO$_2$] computed at step 122 and the deoxygenated hemoglobin concentration [Hb] computed at step 124.

At step 128, the derived oxygenated hemoglobin concentration [HbO$_2$], deoxygenated hemoglobin concentration [Hb], and oxygen saturation $S_tO_2$ are output to the output unit 22, and the measuring processing routine is ended.

As explained above, according to the optical measuring device of the first exemplary embodiment, a first specific distance corresponding to the thickness of the intervening layer is computed based on a relationship between the thickness of the intervening layer, the first specific distance that is a short source-detector source-receiver distance, and the measurement sensitivity of a surface layer and the measurement sensitivity of a deep layer, and a second specific distance corresponding to the thickness of the intervening layer is computed based on a relationship between the thickness of the intervening layer, the second specific distance that is a long source-detector source-receiver distance, and the measurement sensitivity of the intervening layer and the measurement sensitivity of a deep layer. A source-detector source-receiver distance can accordingly be computed for accurately measuring the light absorbance of a deep layer such as the uterine muscle. Moreover, since the source-detector source-receiver distance for accurately measuring the light absorbance of deep layer tissue in a human body can be computed, the light absorbance in the deep layer can also be computed with good precision.

Tissue at deep sites such as the uterine muscle has the following issues for resolution. Consider a case that tries to measure tissue of at a deeper site when there is a split into a surface layer, an intermediate layer and a deep layer, the light path length of the deep site becomes much smaller than that in the surface layer and intermediate layer tissue, and so data from even a small amount of blood in the intermediate fat has an influence as a cause of error. In a conventional method, due to measurements being made on standard muscle, it is possible to correct for data relating to the upper fat layer, however in cases such as uterine muscle that try to measure tissue in a deeper layer, correction is not only required for the fat thickness, but also for the influence of the absorption coefficient of the fat. The present exemplary embodiment therefore derives the uterine muscle absorption coefficient $\mu_{au}$ using the $S_{far}$–$\mu_{au}$ curve corresponding to the fat thickness and the fat absorption coefficient, then derives the oxygenated hemoglobin concentration and deoxygenated hemoglobin concentration, the oxygen saturation, of the uterine muscle based thereon. Accurate oxygenated hemoglobin concentration and deoxygenated hemoglobin concentration, the oxygen saturation, can accordingly be obtained that have been corrected for the influence of the fat thickness and the fat absorption coefficient, thereby enabling a large improvement in the ability to quantify these factors.

Conventionally it was not possible to obtain biochemical data indicating the condition of the uterine muscle non-invasively. However, according to the present exemplary embodiment, the condition of the uterine muscle can be measured non-invasively, enabling its use as a barometer as to whether or not labor pains are occurring normally. Moreover, evaluation and diagnosis can be made quantitatively for too strong labor pains or feeble labor pains, fatigue, or a state in which natural contractions are not liable to occur.

There are various existing techniques for measuring the optical characteristics of a deep site in a multi-layer structure medium. However, in attempts to measure optical characteristics of deep sites below multi-layers, since the strength of a signal of the medium of interest varies greatly with sensor placement, source-detector source-receiver distance setting to obtain a more effective signal is conventionally performed by experience without any particular evidence, or based on the rough and ready rule of setting measuring at a depth of about half the source-detector source-receiver distance. However, according to the present exemplary embodiment, due to being able to determine the optimum sensor placement with a fixed procedure, the source-detector source-receiver distance computation method in the present exemplary embodiment is extremely beneficial in raising the measurement precision of deeper sites.

Explanation next follows regarding a second exemplary embodiment. Note that the configuration of an optical measuring device according to the second exemplary embodiment is similar to that of the first exemplary embodiment, and so explanation thereof will be omitted.

The second exemplary embodiment differs from the first exemplary embodiment in that the fat thickness measured by a fat thickness measurement device is directly input to the optical measuring device.

In the optical measuring device according to the second exemplary embodiment, a fat thickness measurement device, not illustrated in the drawings, is connected to the optical measuring device according to the second exemplary embodiment, and the thickness of fat of the measurement subject that has been measured by the fat thickness measurement device is directly input thereto.

During measurement, the measurement subject fat thickness is measured by the fat thickness measurement device, and the measurement result is input to the optical measuring device. The probe 12 is then placed in contact with the abdominal region of the measurement subject, and measurement start is instructed by operating the operation unit 18, and steps 106 onwards of the measuring process routine explained above for the first exemplary embodiment are executed.

Note that other parts of the configuration and operation of the optical measuring device according to the second exemplary embodiment are similar to those of the first exemplary embodiment and so further explanation thereof is omitted.

Note that although explanation has been given in the above exemplary embodiment of an example in which the fat thickness is being measured by the fat thickness measurement device, there is no limitation thereto. For example, configuration may be made such that the thickness of a fat layer is computed by a doctor by looking at an image on an ultrasound imaging apparatus, and a numerical value is input by operating the operation unit 18. Moreover, configuration may be made using a simple measurement implement such as a caliper to measure the fat thickness of the measurement subject, with this then input by operation of the operation unit 18.

Explanation next follows regarding a third exemplary embodiment. Note that portions that are of similar configuration to the first exemplary embodiment are allocated the same reference numerals and further explanation thereof is omitted.

The third exemplary embodiment differs from the first exemplary embodiment in the point that the PD is moved according to the computed source-detector source-receiver distance.

The optical measuring device according to the third exemplary embodiment is equipped with four PDs 26 and the position of the PDs 26 is changed by moving with a movement mechanism.

In the optical measuring device according to the third exemplary embodiment, at step 100 of the measuring process routine explained in the first exemplary embodiment, the four PDs 26 are moved by the movement mechanism so as to adopt light reception positions corresponding to the source-detector source-receiver distances $\rho$ 1-1, $\rho$ 1-2, $\rho$ 2-1 and $\rho$ 2-2 that enable efficient detection of the thickness of fat.

Moreover, at step 110, two PDs 26 are moved to light reception positions corresponding to the source-detector source-receiver distance $\rho$ 1-1, $\rho$ 1-2 computed at step 106, and two PDs 26 are moved to light reception positions corresponding to the source-detector source-receiver distance $\rho$ 2-1, $\rho$ 2-2 computed at step 108.

Note that other parts of the configuration and operation of the optical measuring device according to the third exemplary embodiment are similar to those of the first exemplary embodiment, and so further explanation thereof is omitted.

Note that although explanation has been given in the above exemplary embodiment of a case in which the PDs are moved by the movement mechanism, there is no limitation thereto, and configuration may be made such that the PDs are moved manually so as to be positioned at the computed source-detector source-receiver distances.

Explanation next follows regarding a fourth exemplary embodiment. Explanation in the fourth exemplary embodiment is of a case in which the present invention is applied to an optical measuring device for measuring the sugar content in fruit. Note that the configuration of the optical measuring device according to the fourth exemplary embodiment is similar to that of the first exemplary embodiment, and so further explanation is omitted.

In an optical measuring device according to the fourth exemplary embodiment, light is illuminated from the LED 24 at wavelengths $\lambda 1$ and $\lambda 2$ that are appropriate for measuring the absorption coefficient of light by glucose.

Moreover, as a source-detector source-receiver distance between the LED 24 and the PDs 26, a distance is computed that is appropriate for the thickness of the external skin and internal skin of the fruit.

Figure 14:
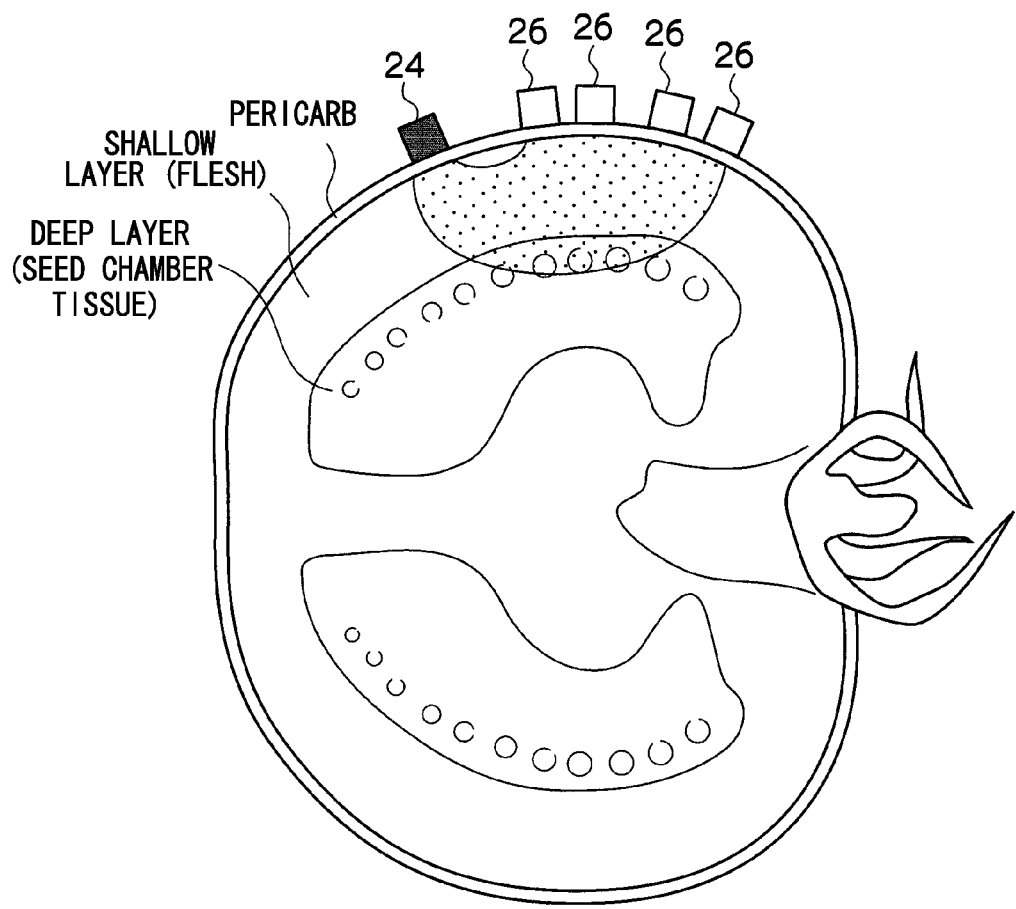
FIG. 14 is an illustration of a case in which the measurement target object is a fruit.

For example, as illustrated in FIG. 14, in cases in which the measurement target object is a fruit such as a tomato, there is a layered structure with a pericarb, flesh, and jelly-like seed chamber tissue. According to the optical measuring device, measurement is performed with separation between data of the flesh of a shallow layer, and data of seed chamber tissue of a deep layer.

In the measuring process routine according to the fourth exemplary embodiment, four predetermined PDs 26 are selected at the light reception position corresponding to source-detector source-receiver distances ρ 1-1, ρ 1-2, ρ 2-1, ρ 2-2 that are capable of efficiently detecting the flesh thickness. Then an instruction it given to the LED driver 32 to emit light from the LED 24, and the light intensity of the light received by the four selected PDs 26 is acquired from the amplifier 36.

Then the flesh thickness is computed based on the acquired light intensity of light received by the four PDs 26.

Next, the short source-detector source-receiver distance ρ 1-1 is computed according to Equation (7) based on the computed flesh thickness, and the ρ 1-2 is computed. Then based on the above computed flesh thickness, the long source-detector source-receiver distance ρ 2-1 is computed according to Equation (8), and the ρ 2-2 is computed.

Next two PDs 26 are selected at light reception positions corresponding to the computed source-detector source-receiver distance ρ 1-1, ρ 1-2, and two PDs 26 are selected at light reception positions corresponding to the computed source-detector source-receiver distance ρ 2-1, ρ 2-2.

Then the LED driver 32 is instructed to emit light from the LED 24, and the light intensity of light received by the four selected PDs 26 is acquired from the amplifier 36. Note that light is emitted in the sequence of the first wavelength λ1 then the second wavelength λ2, and the respective light intensities acquired.

Next, based on the measured light intensities of the first wavelength λ1 and the second wavelength λ2, spatial slopes $S_{near}$ of the first wavelength λ1 and the second wavelength λ2 are computed according to Equation (1), and then spatial slopes $S_{far}$ of the first wavelength λ1 and the second wavelength λ2 are computed according to Equation (2).

Then parameters are read from the memory 20, and then based on the spatial slope $S_{near}$ of the derived first wavelength λ1 and the second wavelength λ2, the absorption coefficients for the first wavelength λ1 and the second wavelength λ2 are computed using the parameters according to the relationship equation between the spatial slope $S_{near}$ and the flesh absorption coefficient.

The values of parameters of the relationship equation between the spatial slope $S_{far}$ and the seed chamber tissue absorption coefficient corresponding to the combination of the computed flesh thickness and the computed absorption coefficients of the first wavelength λ1 and the second wavelength λ2 are read from the memory 20.

Then based on the derived spatial slope $S_{far}$ of the first wavelength λ1 and the second wavelength λ2, the parameters that have been read are then used to compute the seed chamber tissue absorption coefficients of the first wavelength λ1 and the second wavelength λ2 according to the relationship equation between the spatial slope $S_{far}$ and the seed chamber tissue absorption coefficient.

Then based on the derived flesh absorption coefficient and the seed chamber tissue absorption coefficient, the sugar content of the flesh and the seed chamber tissue is derived, and the derived sugar content is then output to the output unit 22.

As explained above, according to the optical measuring device of the fourth exemplary embodiment, the first specific distance corresponding to the intervening layer thickness is computed based on a relationship between a thickness of an intervening layer down to the seed chamber tissue, a first specific distance that is a short source-detector source-receiver distance, and a measurement sensitivity of a surface layer and a measurement sensitivity of a deep layer (the seed chamber tissue). The second specific distance corresponding to the intervening layer thickness is computed based on a relationship between the intervening layer thickness, a second specific distance that is a long source-detector source-receiver distance, and the intervening layer measurement sensitivity and the measurement sensitivity of the deep layer. Source-detector source-receiver distances can accordingly be computed that are appropriate to accurate light absorbance measurement of the deep layer such as the seed chamber tissue. Moreover, due to be able to calculate source-detector source-receiver distances appropriate for accurately measuring the light absorbance of deep layer tissue of a fruit, the light absorbance in the deep layer can be computed with good precision.

There is an existing non-destructive measuring method for fruit sugar level described in Patent Document (Japanese Patent 2517858). Although this method corrects for the influence from the pericarb thickness, the internal structure is treated as being uniform. Thus the non-uniform nature is a cause of a drop in precision and it is difficult to separate data for the flesh and the seed chamber tissue. Moreover, there has not been a procedure up to now capable of acquiring separate data for each layer by considering a layered structure of the measurement object in optical measuring methods of horticultural products. However, according to the present exemplary embodiment, non-destructive measurement is possible that separates data such as sugar content for each of the layers with horticultural products with a complicated structure as the measurement object.

Note that although explanation has been given in the above exemplary embodiment of an example in which the sugar content is computed of the flesh portion and the seed chamber tissue, there is no limitation thereto, and configuration may be made in which the color of the flesh portion and the seed chamber tissue is derived.

Explanation next follows regarding a fifth exemplary embodiment. Note that portions of similar configuration to those of the first exemplary embodiment are allocated the same reference numerals, and further explanation thereof is omitted.

The fifth exemplary embodiment differs from the first exemplary embodiment in the points that plural LEDs are provided and that the LEDs are selected according to the computed source-detector source-receiver distances.

In an optical measuring device according to the fifth exemplary embodiment, plural LEDs 24 and a photodiode (PD) 26 are provided in a probe 12.

Each of the LEDs 24 are placed with a different respective source-detector source-receiver distance to the PD 26, with the plural LEDs 24 placed for example in a row with a specific spacing.

A selection circuit 33 is instructed by the controller 16 to select four of the LEDs 24, and to make the selected four LEDs 24 emit light in sequence. When this is performed the output from the PD 26 is sequentially output to the I-V converter 34.

The controller 16 instructs the selection circuit 33 to select the four LEDs 24 in sequence, and instructs the LED driver 32 to emit light sequentially from the selected LEDs 24. Then the hemoglobin concentration is computed as follows based on the light intensities of light received by the PD 26 as a result.

Note that other parts of the configuration and operation of the optical measuring device according to the fifth exemplary embodiment are similar to those of the first exemplary embodiment and so further explanation is omitted.

Note that configuration may be made in the above first exemplary embodiment to fifth exemplary embodiment such that the position of the probe 12 is moved, and measurements are performed at each of the positions, with an average thereof taken as the final measurement result.

Moreover, although explanation has been given in the first exemplary embodiment to the fourth exemplary embodiment of an example in which the PDs are arrayed in a row, there is no limitation thereto. For example configuration may be made with the PDs arranged in a circular shape with the position of the LED at the center. In such cases, the PDs may be arranged in plural circular shapes of different radius as the source-detector source-receiver distances. Moreover, plural combinations may be taken of the PDs, measurements performed, and an average thereof taken as the final measurement result.

Moreover, although explanation has been given in the fifth exemplary embodiment of an example in which the LEDs are arrayed in a row, there is no limitation thereto. For example configuration may be made with the LEDs arranged in a circular shape with the position of the LED at the center. In such cases, the LEDs may be arranged in plural circular shapes of different radius as the source-detector source-receiver distances. Moreover, plural combinations may be taken of the LEDs, measurements performed, and an average thereof taken as the final measurement result.

Moreover, although explanation has been given in the first exemplary embodiment to the fifth exemplary embodiment of examples of optical measuring devices equipped with a function of a distance computation device, configuration may be made with an optical measuring device and a distance computation device configured as separate devices. In such cases, the source-detector source-receiver distance computed by the distance computation device may be input to the optical measuring device.

Moreover, there is no limitation to a biological body, and the present invention may be applied to another object as long as light reaches as far as internal matter.

EXPLANATION OF THE REFERENCE NUMERALS

10 optical measuring device
12 probe
14 driving device
16 controller
18 operation unit
20 memory
24 LED
26 PD
32 LED driver
33 selection circuit

The invention claimed is:
1. An optical measuring device comprising:
a light emitting component comprising a light source configured to emit each of two different wavelengths of light, wherein the light emitting component is disposed within the optical measuring device to emit light onto a human body when the light emitting component is placed adjacent to the human body;
one or more processors;
a program memory coupled to the one or more processors and storing executable instructions that, when executed by the one or more processors, cause the optical measuring device to:
implement an acquisition unit that acquires a thickness of a skin and fat layer of the human body;
implement a first computation unit that computes a first specific distance corresponding to the acquired thickness of the skin and fat layer based on a predetermined relationship between the thickness of the skin and fat layer, the first specific distance, and a measurement sensitivity of the skin and a measurement sensitivity of a uterine muscle layer of the human body when light from the light emitting component is received at a position the first specific distance away from the light source; and
implement a second computation unit that computes a second specific distance corresponding to the acquired thickness of the skin and fat layer based on a predetermined relationship between the thickness of the skin and fat layer, the second specific distance, and a measurement sensitivity of the skin and fat layer and a measurement sensitivity of the uterine muscle layer when light from the light emitting components is received at a position the second specific distance away from the light source;
a light reception component comprising a plurality of photodetectors positioned at a plurality of distances from the light source, the light reception component configured to:
receive light at the position the computed first specific distance away from the light source out of the light emitted from the light source, wherein the light has at least passed through the skin and fat layer,
receive light at a different position from the first specific distance away position out of the light emitted from the light source, wherein the light has at least passed through the skin and fat layer,
receive light at the position the computed second specific distance away from the light source out of the light emitted from the light source, wherein the light has at least passed through the skin and fat layer and the uterine muscle layer, and
receive light at a different position from the second specific distance away position out of the light emitted from the light source, wherein the light has at least passed through the skin and fat layer and the uterine muscle layer;
wherein the program memory further stores executable instructions that, when executed by the one or more processors, cause the optical measuring device to:
implement a spatial slope computation unit that, for each of the two wavelengths, computes a first spatial slope based on light intensities of light respectively received at the first specific distance away position and at the different position from the first specific distance away position, and that computes a second spatial slope based on light intensities of light respectively received at the second specific distance away position and at the different position from the second specific distance away position; and
implement an absorption computation unit that for each of the two wavelengths, computes a light absorbance in the uterine muscle layer based on the computed first spatial slope, the computed second spatial slope, and a thickness of the skin and fat layer, and that, based on the light absorbance in the uterine muscle layer for each of the two wavelengths, computes a concentration of at least one of oxygenated hemoglobin or deoxygenated hemoglobin of the uterine muscle; and an output component configured to receive and present one or more of the computed concentration of the at least one of the oxygenated hemoglobin or deoxygenated hemoglobin of the uterine muscle.

2. The optical measuring device of claim 1, wherein:

the first specific distance is a distance corresponding to the thickness of the skin and fat layer derived based on a predetermined relationship between the thickness of the skin and fat layer, the first specific distance, and the measurement sensitivity of the skin and the measurement sensitivity of the uterine muscle layer when light from the light emitting unit is received at the first specific distance away position; and the second specific distance is a distance corresponding to the thickness of the skin and fat layer derived based on a predetermined relationship between the thickness of the skin and fat layer, the second specific distance, and a measurement sensitivity of the skin and fat layer and a measurement sensitivity of the uterine muscle layer when light from the light emitting unit is received at the second specific distance away position.

3. The optical measuring device of claim 1, wherein the first computation unit computes the first specific distance corresponding to the acquired thickness of the skin and fat layer based on the first specific distance predetermined for each of the thicknesses of the skin and fat layer where the measurement sensitivity of the skin and the measurement sensitivity of the uterine muscle layer match each other.

4. The optical measuring device of claim 1, wherein the first computation unit computes the first specific distance corresponding to the acquired thickness of the skin and fat layer based on a relationship equation expressing a relationship between the thickness of the skin and fat layer and the first specific distance where the measurement sensitivity of the skin and the measurement sensitivity of the uterine muscle layer match each other.

5. The optical measuring device of claim 1, wherein the second computation unit computes as the second specific distance a distance corresponding to a distance where a coefficient of variance is at a minimum in the acquired thickness of the skin and fat layer and a distance further away than the distance where the coefficient of variance is at the minimum, based on a predetermined relationship for each of the thicknesses of the skin and fat layer between the second specific distance and the coefficient of variance of a ratio of the measurement sensitivity of the skin and fat layer and a measurement sensitivity of the uterine muscle layer.

6. The optical measuring device of claim 5, wherein the second computation unit computes the second specific distance corresponding to the acquired thickness of the skin and fat layer based on a relationship equation expressing a relationship between the thickness of the skin and fat layer, and the distance corresponding to a distance where the coefficient of variance of the ratio of the measurement sensitivity of the skin and fat layer and the measurement sensitivity of the uterine muscle layer is at a minimum, and the distance further away than the distance where the coefficient of variance of the ratio is at a minimum.

7. The optical measuring device of claim 1, wherein:

the light reception unit comprises a plurality of light receptors that receive the light emitted by the light emitting unit at a plurality of positions that differ from each other in distance away from the light emitting unit;

light is received by the light receptor selected, from out of the plurality of light receptors, to correspond to the first specific distance computed by the first computation unit, and light is received by the light receptor selected to correspond to the different position from the first specific distance away position; and light is received by the light receptor selected, from out of the plurality of light receptors, to correspond to the second specific distance computed by the second computation unit, and light is received by the light receptor selected to correspond to the different position from the second specific distance away position.

8. The optical measuring device of claim 1, wherein:

the light emitting unit comprises a plurality of light illuminating portions that illuminate light onto the measurement target object;

light is illuminated from the light illuminating portion selected, from out of the plurality of light illuminating portions, to correspond to the first specific distance computed by the first computation unit, and light is illuminated from the light illuminating portion selected to correspond to the different position from the first specific distance away position; and light is illuminated from the light illuminating portion selected, from out of the plurality of light radiating illuminating portions, to correspond to the second specific distance computed by the second computation unit, and light is illuminated from the light illuminating portion selected to correspond to the different position from the second specific distance away position.

9. The optical measuring device of claim 1, wherein the acquisition unit acquires a thickness of the skin and fat layer measured using an ultrasound imaging apparatus.

10. The optical measuring device of claim 1, wherein the acquisition unit computes the thickness of the skin and fat layer based on the first spatial slope and the second spatial slope that have been computed at four different distances respectively predetermined as the first specific distance, a distance to the different position from the first specific distance away position, the second specific distance, and a distance to the different position from the second specific distance away position.

11. The optical measuring device of claim 1, further comprising:

a storage unit storing computation parameters for computing light absorbance in the uterine muscle layer for each combination of thickness of the skin and fat layer and light absorbance in the skin and fat layer; wherein, the absorption computation unit computes the light absorbance of the skin and fat layer based on the first spatial slope, reads the computation parameters corresponding to the acquired thickness of the skin and fat layer and the light absorbance in the skin and fat layer from the storage means, and computes the light absorbance in the uterine muscle layer based on the read computation parameters and the second spatial slope.

12. The optical measuring device of claim 1, wherein the absorption computation unit computes the concentration of the oxygenated hemoglobin and the deoxygenated hemoglobin, and computes the oxygen saturation based on the computed concentrations of the oxygenated hemoglobin and the deoxygenated hemoglobin.

\* \* \* \* \*